United States Patent
Bowles, Sr. et al.

[11] Patent Number: 5,183,994
[45] Date of Patent: Feb. 2, 1993

[54] HEATED DRUG BOX

[76] Inventors: Dale D. Bowles, Sr., 2443 Hemlock Ave.; Charles L. Parmley, 23 Kelley, both of Granite City, Ill. 62040

[21] Appl. No.: 605,114

[22] Filed: Oct. 26, 1990

[51] Int. Cl.⁵ .................................... H05B 3/00
[52] U.S. Cl. .................... 219/387; 219/521; 219/386
[58] Field of Search .............. 219/385, 386, 387, 521

[56] References Cited

U.S. PATENT DOCUMENTS

| | | | |
|---|---|---|---|
| 1,297,281 | 3/1919 | Wheeler | 219/521 |
| 1,669,192 | 5/1928 | Fischer | 219/386 |
| 1,683,889 | 9/1928 | Hayne | 219/202 |
| 1,979,222 | 10/1934 | Goodwin | |
| 2,196,035 | 4/1940 | Shaw | 219/286 |
| 2,515,514 | 7/1950 | Jones | 219/385 |
| 3,515,119 | 6/1970 | Kivela | 219/387 |
| 3,549,861 | 12/1970 | Trachtenberg | 219/387 |
| 3,624,346 | 11/1971 | Guth | 219/201 |
| 3,808,401 | 4/1974 | Wright | 219/387 |
| 4,037,081 | 7/1977 | Aldridge | 219/387 |
| 4,163,896 | 8/1979 | McAvinn | 219/386 |
| 4,206,343 | 6/1980 | Mousel | 219/387 |
| 4,233,495 | 11/1980 | Scoville | 219/386 |
| 4,495,402 | 1/1985 | Burdick | 219/521 |
| 4,523,078 | 6/1985 | Lehmann | 219/386 |
| 4,543,471 | 9/1985 | Anderson | 219/387 |
| 4,621,633 | 11/1986 | Bowles | 128/203.17 |

Primary Examiner—Teresa J. Walberg
Attorney, Agent, or Firm—Grace J. Fishel

[57] ABSTRACT

A heated drug box for transporting emergency drugs and I. V. solutions at a safe working temperature wherein the medical supplies usually required first are accessible in a side compartment through door means in the side of the box. Other door means are provided in the top of the box through which a main compartment is accessible. The side and main compartments are in thermal contact with a heater means located between the side and main compartments for heating the contents of the box to a safe working temperature.

6 Claims, 2 Drawing Sheets

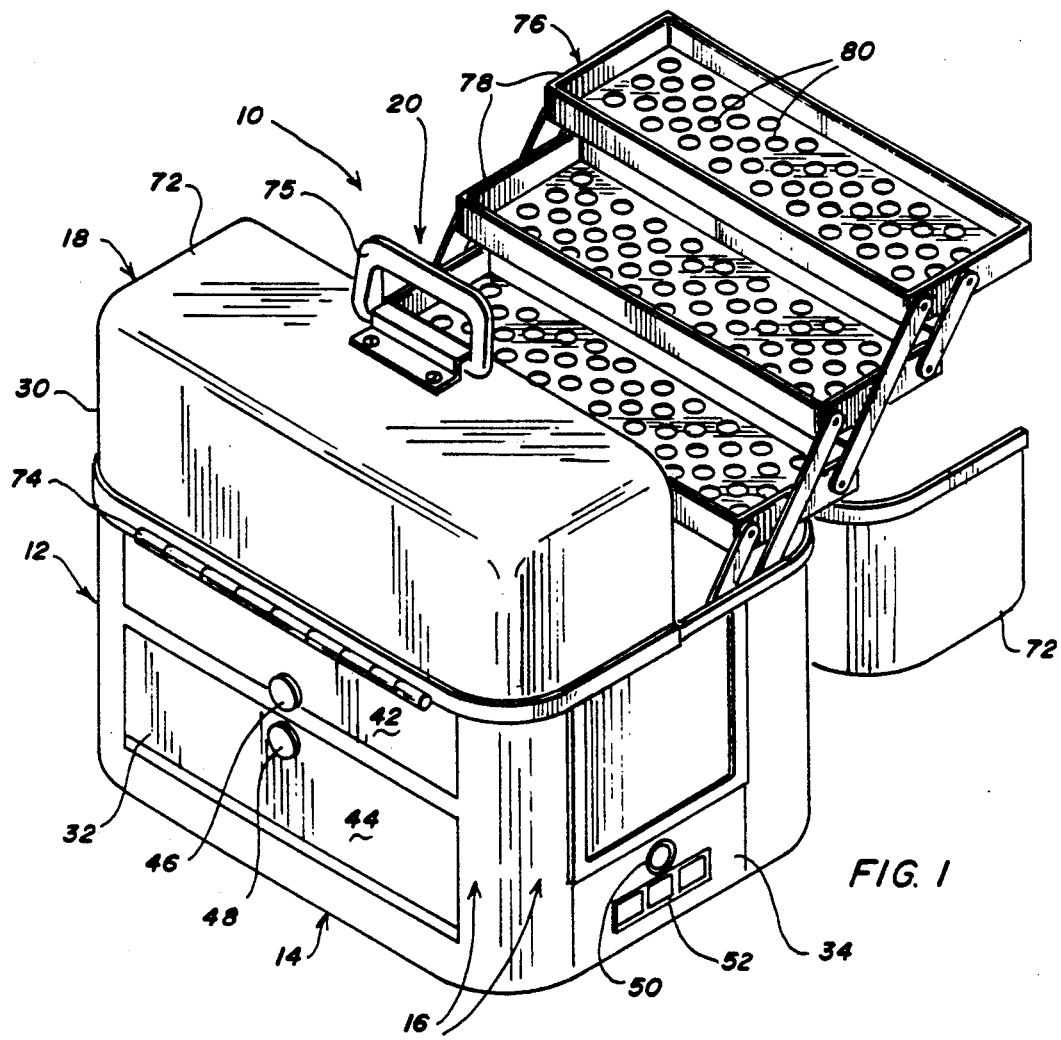
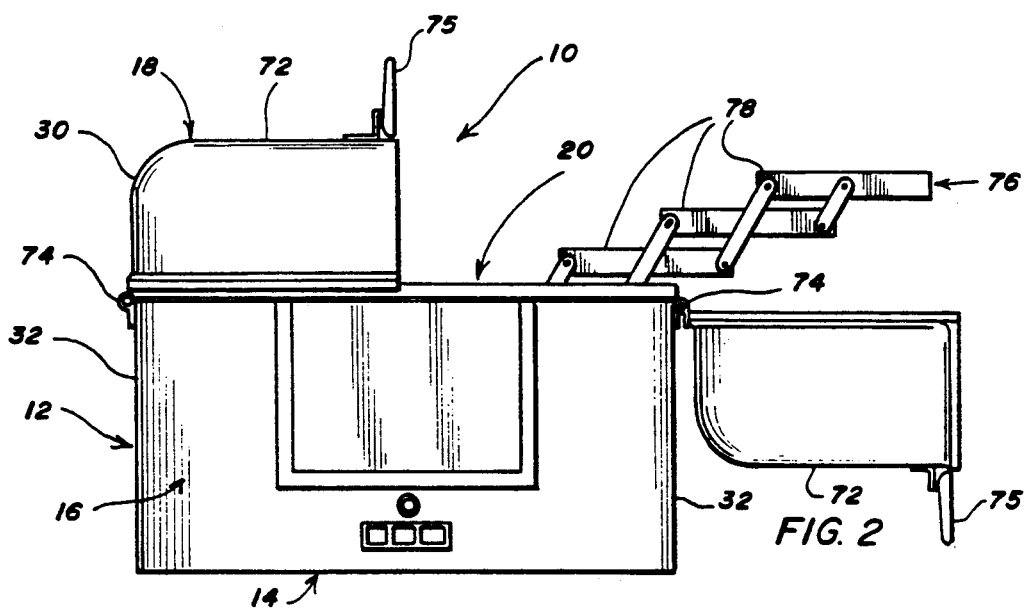

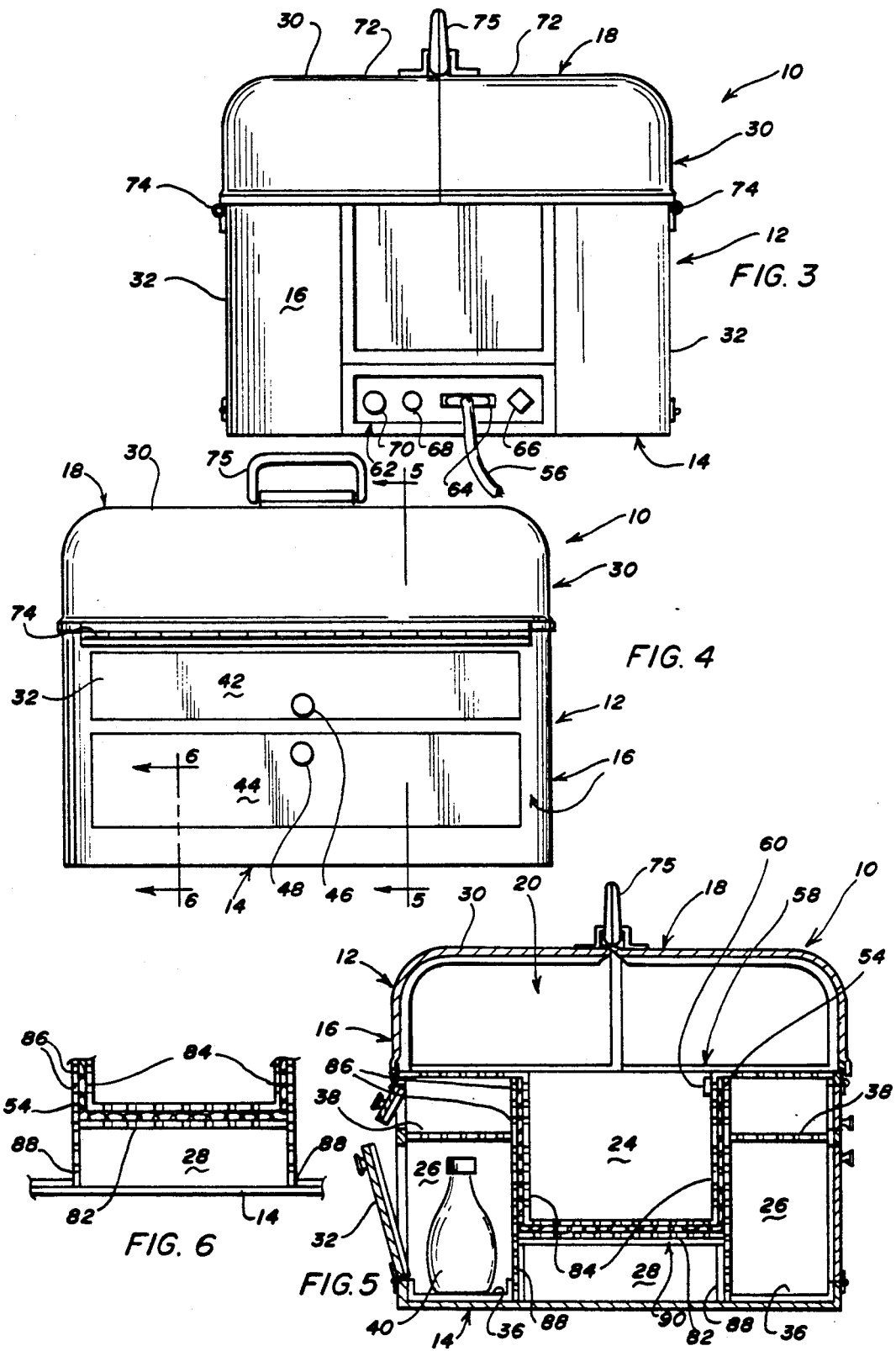

HEATED DRUG BOX

The present invention relates to a heated drug box for transporting emergency drugs and I. V. solutions at a safe working temperature wherein the medical supplies usually required first are accessible through door means in the side of the box.

BACKGROUND OF THE INVENTION

Drug boxes are designed to be carried by an emergency care giver to a victim suffering a medical emergency and used under cramped conditions in helicopters, ambulances, boats and other types of mobile emergency vehicles. In many instances, treatment of the victim must be rendered under hostile conditions, one element of which may be cold temperatures.

When the weather is cold, it is important that the medical supplies carried in the drug box be kept at working temperature. For example, I. V. solutions used to treat the victim for shock or loss of blood should be administered at near body temperature to prevent further core temperature drop during treatment. It is also necessary to keep other medical supplies warm to maintain their effectiveness.

The heated drug boxes known in the past have a heated main compartment accessible through a hinged top. When the medical supplies usually required first (i. e., I. V. solutions) are removed, all of the other medical supplies are exposed to the environment (e. g., rain, theft and other hostile conditions). In addition, it is difficult to open the drug box wide enough under cramped conditions to get the necessary medical supplies out.

In view of the above, there is a need for a heated drug box for transporting emergency drugs and I. V. solutions wherein the medical supplies usually required first are easily accessible without opening up the box entirely. It is therefore an object of the present invention to provide a heated drug box wherein medical supplies usually required first are accessible through door means in the side of the box. Other objects and features of the invention will be in part apparent and in part pointed out hereinafter, the scope of the invention being indicated by the subjoined claims.

SUMMARY OF THE INVENTION

A heated drug box for transporting drugs and I. V. solutions at a safe working temperature has an insulated case with a bottom, side walls and a top enclosing an interior space. The interior space is divided into a main compartment and a side compartment. The main compartment and the side compartment are in thermal contact with a heater means which can be connected to a power source under control of a temperature control means. The main compartment is accessible through a first door means in the top of the case and the side compartment is accessible through a second door means in the side of the case. The side compartment is adapted for storage of I. V. solutions and is accessible without otherwise opening the drug box to the environment.

BRIEF DESCRIPTION OF THE DRAWINGS

In the accompanying drawings, in which one of various possible embodiments of the invention is illustrated, corresponding reference characters refer to corresponding parts throughout the several views of the drawings in which:

FIG. 1 is a perspective view of a heated drug box in accordance with the present invention with one side of the top wide open;

FIG. 2 is a right end view of the heated drug box as shown in FIG. 1;

FIG. 3 is a left end view of the heated drug box as shown in FIG. 1 but with both sides of the top closed;

FIG. 4 is a side elevational view of the heated drug box as shown in FIG. 3;

FIG. 5 is a sectional view taken along line 5—5 in FIG. 4; and, 10 FIG. 6 is a sectional view taken along line 6—6 in FIG. 4.

DETAILED DESCRIPTION OF THE INVENTION

Referring to the drawings more particularly by reference number, a heated drug box 10 for transporting drugs and I. V. solutions at a safe working temperature comprises an insulated case 12. Insulated case 12 has a bottom 14, side walls 16 and a top 18 enclosing an interior space 20. Interior space 20 is divided into a main compartment 24, side compartments 26 and a bottom compartment 28. Bottom compartment 28 is located under main compartment 24 and between side compartments 26. Main compartment 24 is accessible through a first door means 30 in top 18, side compartments 26 are accessible through second door means 32 in side walls 16 and bottom compartment 28 is accessible through a third door means 34 in side walls 16.

Side compartments 26 are adapted for storage of I. V. solutions which can be reached through second door means 32 without opening first door means 30 in top 18. As shown in FIG. 5, side compartments 26 are illustrated divided into a lower tier 36 and an upper tier 38. Upper tier 38 is adapted for storage of equipment needed to administer I. V. fluid such as I. V. tubing, needles, gauze pads, tape, topical ointment, alcohol and so forth, generally described as I. V. supplies. Lower tier 36 is adapted for storage of containers 40 (i. e., bags, bottles or the like) of infusion solutions. Second door means 32 is divided into an upper section 42 (through which the supplies in upper tier 38 are accessed) and a lower section 44 (through which the supplies in lower tier 36 are accessed). Upper section 42 and lower section 44 are held closed with an upper latch 46 and a lower latch 48, respectively.

Bottom compartment 28 is adapted for storage of controlled substances such as narcotics. Third door means 34 includes a bottom latch 50 and a lock 52, shown for illustration purposes as a combination lock.

Main compartment 24, side compartments 26 and bottom compartment 28 are in thermal contact with a heater means 54 connected to a power source 56 under control of a temperature control means 58 including a temperature probe 60 in main compartment 24. Heater means 54 can be an electrically heated belt or the like. Thermal contact includes heat exchange by conduction, convention and radiation, in order of declining importance. Power source 56 can be either alternating or direct current. A control panel 62 on one of side walls 16 includes a socket 64 to plug in power source 56, a power fuse 66, a power on light 68 to show when power is being supplied by power source 56 and a cycle light 70 to show when heater means 54 is on. It will be understood that power source 56 can also be a battery carried in insulated case 12. Depending on the requirements of heater means 54, suitable components can be included in temperature control means 58 to step the voltage up or down and/or to convert between AC and DC current.

As illustrated in the drawings, first door means 30 in top 18 are divided into center opening sections 72 forming a dome hinged at 74 on opposite side walls 16 of insulated case 12. A suitable latch and carrying handle 75 holds center opening sections 72 closed and provides a means by which insulated case 12 can be carried. A pair of cantilevered trays 76 shown with multiple levels 78 are mounted under the dome formed by center opening sections 72, above main compartment 24 and side compartments 26 and on opposite side walls 16 of insulated case 12. Pair of cantilevered trays 76 are in thermal contact with main compartment 24 and side compartments 26. Pair of cantilevered trays 76 preferably have perforated bottoms 80 for better thermal contact with main compartment 24 and side compartments 26.

As described above, bottom compartment 28 is located under main compartment 24 and between side compartments 26. More particularly, as shown in FIG. 5, bottom compartment 28 borders main compartment 24. Side compartments 26 border main compartment 24 and bottom compartment 28. Heater means 54 are contained in a wall 82 forming the border between bottom compartment 28 and main compartment 24 and a pair of opposing walls 84 forming the border between side compartments 26 and main compartment 24. Wall 82 and pair of opposing walls 84 are preferably formed of a thermally conductive material and are perforated at 86 for more effective heat exchange with heater means 54.

An extension 88 of pair of opposing walls 84 divide side compartments 26 from bottom compartment 28. Bottom compartment 28 is preferably divided into an insulated section 90 located behind control panel 62 to avoid overheating of temperature control means 58 by heater means 54. As seen in FIG. 6, however, extension 88 of pair of opposing walls 84 are perforated at 86 for better heat exchange between bottom compartment 28 and side compartments 26.

In use, emergency drugs and I. V. solutions suitable for use by an emergency care giver are stored in heated drug box 10. Containers 40 of infusion solutions are preferably stored in lower section 44 of side compartments 26 and I. V. supplies are stored in upper section 42. Pair of cantilevered trays 76 are filled with smaller items and main compartment 24 with larger items. Controlled substances are placed in bottom compartment 28 under security of lock 52.

The contents of heated drug box 10 are maintained at a safe working temperature by heater means 54 which is powered by power source 56. Overheating is avoided by temperature control means 58 which maintains the temperature in the box in a range from about 90 to 105 degrees F (more preferably in a range from about 95 to 100 degrees F) measured by temperature probe 60. Since heated drug box 10 is insulated, it will maintain the temperature of the supplies at a safe working temperature after the box is disconnected from power source 56 for an appreciable period of time. This allows heated drug box 10 to be carried to the victim or to be used in an emergency vehicle or the like which is not capable of serving as a source of power.

When needed, the items usually required first (i. e., I. V. solutions and supplies) are accessible through the sides of the heated drug box 10 without requiring first door means 30 in top 18 to be opened. This is a major improvement over prior art heated drug boxes which require that the box be opened wide. Heated drug box 10 is well suited for use in police cars and other vehicles (or circumstances) where space is at a premium.

Narcotics must be accounted for by emergency personnel and may be stolen in a hostile environment while the care giver is engaged in rendering emergency treatment. Heat drug box 10 provides required security for the controlled substances locked in bottom compartment 28.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed is:

1. A heated drug box for transporting drugs and I. V. solutions at a safe working temperature comprising an insulated case having a bottom, sidewalls and a top enclosing an interior space partitioned into a main compartment, a pair of side compartments and a bottom compartment, said compartments being in thermal contact with each other but being separated by physical barriers, said side compartments bordering the main compartment and said main compartment positioned over and bordering the bottom compartment, said compartments being in thermal contact with a heater means connected to a power source under control of a temperature control means, said main compartment being accessible through a first door means in the top, each of said side compartments being accessible through a second door means in the sidewalls and sized for storage of I. V. solution containers and said third compartment being accessible through a third door means in the sidewalls.

2. The heated drug box of claim 1 wherein the heater means is contained in walls forming border between the bottom compartment and the main compartment and between the side compartments and the main compartment, said walls being perforated, conductive and in thermal contact with the heater means whereby the interior space is effectively heated by the heater means.

3. The heated drug box of claim 2 wherein the temperature control means is responsive to a temperature probe in the main compartment.

4. The heated drug box of claim 3 wherein the third compartment is locked whereby the third compartment is made suitable for storage of controlled substances.

5. The heated drug box of claim 4 in which the first door means id divided into two sections hinged on opposite sidewalls of the case and in which a pair of cantilevered trays for storage of smaller items are mounted above the main compartment and the side compartments so that the cantilevered trays are in thermal contact with the main and side compartments.

6. The heated drug box of claim 5 wherein the trays have perforated bottoms for better thermal contact with the main and side compartments.

* * * * *